United States Patent [19]

Jiu et al.

[11] 3,997,401
[45] Dec. 14, 1976

[54] MICROBIAL TRANSFORMATION OF 8-CHLORO-10,11-DIHYDRODIBENZ[B,F][1,4]OXAZEPINE

[75] Inventors: James Jiu; Seth S. Mizuba, both of Morton Grove, Ill.

[73] Assignee: G. D. Searle & Co., Chicago, Ill.

[22] Filed: Dec. 8, 1975

[21] Appl. No.: 638,711

[52] U.S. Cl. .............................. 195/51 R; 260/490
[51] Int. Cl.² ........................................ C12D 13/00
[58] Field of Search ................................. 195/51 R

[56] References Cited
UNITED STATES PATENTS 3,772,151   11/1973   McGahren ...................... 195/51 R

*Primary Examiner*—Alvin E. Tanenholtz
*Attorney, Agent, or Firm*—Barbara L. Cowley; John J. McDonnell

[57] ABSTRACT

8-Chloro-10,11-dihydrodibenz[b,f][1,4]oxazepine is transformed by various microorganisms into compounds having useful pharmacological properties or useful as intermediates in the synthesis of various pharmaceutical compounds. Among the microorganisms useful for this purpose are *Trichoderma lignorum* NRRL 8138, Hormodendrum sp. NRRL 8133, *Cladosporium lignicolum* NRRL 8131, *Hormodendrum cladosporioides* NRRL 8132, *Pullularia pullulans* NRRL 8137, Penicillium sp. NRRL 8136, Mucor sp. NRRL 8135, Chaetomium sp. NRRL 8130, and Hormodendrum sp. NRRL 8134.

2 Claims, No Drawings

MICROBIAL TRANSFORMATION OF 8-CHLORO-10,11-DIHYDRODIBENZ[b,f][1,4]OX-AZEPINE

This invention relates to the microbial transformation process of 8-chloro-10,11-dihydrodibenz[b,f][1,-4]oxazepine by certain microorganisms. More particularly, this invention provides compounds having utility as pharmaceuticals, or as intermediates in the synthesis of other compounds having useful pharmacological properties which are produced by fermenting 8-chloro-10,11-dihydrodibenz[b,f][1,4]oxazepine with *Trichoderma lignorum* NRRL 8138, *Hormodendrum* sp. NRRL 8133, *Cladosporium lignicolum* NRRL 8131, *Hormodendrum cladosporioides* NRRL 8132, *Pullularia pullulans* NRRL 8137, *Penicillium* sp. NRRL 8136, Mucor sp. NRRL 8135, Chaetomium sp. NRRL 8130, and *Hormodendrum* sp. NRRl 8134 in a suitable growth medium.

These NRRL cultures are deposited under conditions such that they are permanently available to the public and may be obtained by writing; ARS Culture Collection, 1815 North University Street, Peoria, Ill., 61604.

The process of the present invention may be carried out in such a manner so as to produce the various transformation products of 8-chloro-10,11-dihydrodibenz[b,f][1,4]oxazepine as shown by the following Scheme A.

NRRL 8133 or enzymes derived therefrom with 8-chloro-10,11-dihydrodibenz[b,f][1,4]oxazepine in a suitable growth medium. One of the resulting products, 8-chloro-10,11-dihydrodibenz[b,f][1,4]oxazepin-11-one, is useful as an intermediate in the synthesis of complex amides of dihydrobenz[b,f][1,4]oxazepine-10-carboxylic acids as described in U.S. Pat. No. 3,357,998. These compounds are useful as anti-hypertensive agents and anti-inflammatory agents. The second product, 2-(2-amino-4-chlorophenoxy)benzyl alcohol, is useful as a smooth muscle antagonist.

The process illustrated as (II) in Scheme A is accomplished by fermenting *Hormodendrum cladosporioides* NRRL 8132 or enzymes therefrom with 8-chloro-10,11-dihydrodibenz[b,f][1,4]oxazepine in a suitable growth medium. The isolated product, 8-chlorodibenz[b,f][1,4]oxazepine is useful as an intermediate in the synthesis of the oxazepine derivatives described in Czechoslovakian Pat. No. 111,215. These compounds possess antihistaminic, antispasmodic, local anesthetic, ataractic, and antidepressive activity. The intermediate product produced in the fermentation medium, 8-chloro-10,11-dihydrodibenz[b,f][1,-4]oxazepin-11-ol, is unstable and not isolated. Its presence, however, is detectable from spectral data.

The process illustrated as (III) in Scheme A may be effected by fermenting *Trichoderma lignorum* NRRL 8138, *Cladosporium lignicolum* NRRL 8131, *Pullularia*

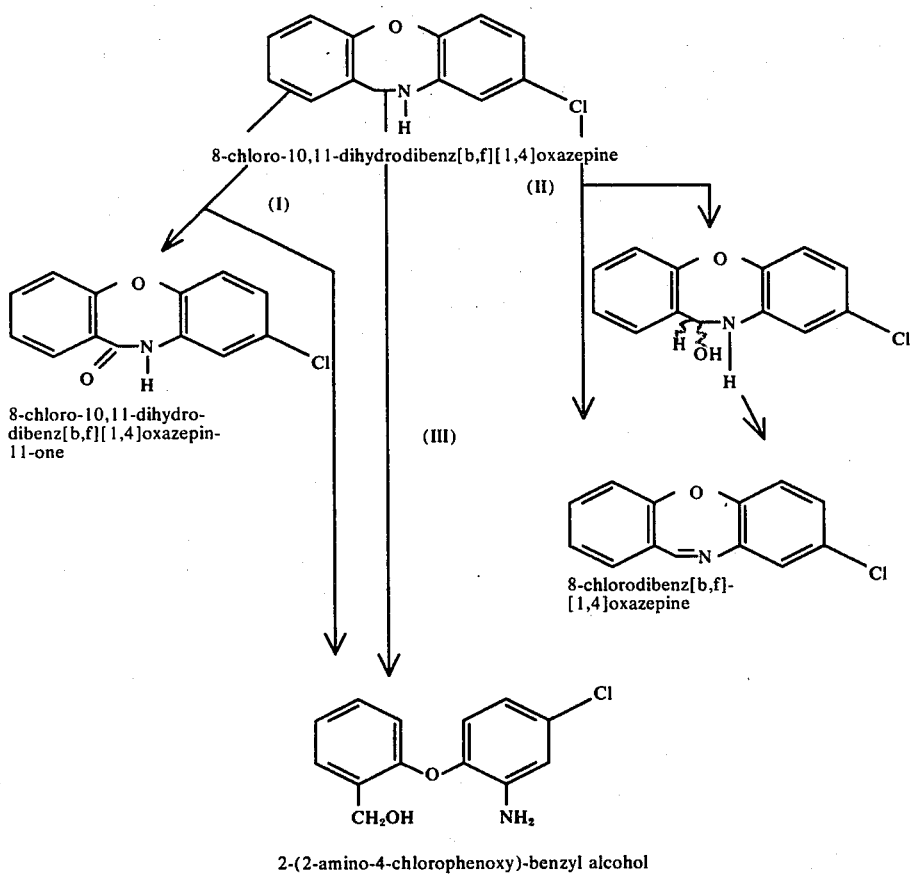

Scheme A 2-(2-amino-4-chlorophenoxy)-benzyl alcohol

The process illustrated as (I) in Scheme A is conveniently effected by fermenting *Hormodendrum* sp.

*pullulans* NRRL 8137, *Penicillium* sp. NRRL 8136, Mucor sp. NRRL 8135, Chaetomium sp. NRRL 8130, or Hormodendrum sp. NRRL 8134, or enzymes derived therefrom with 8-chloro-10,11-dihydrodibenz[b,f][1,4]oxazepine in a suitable growth medium. The resulting novel product, 2-(2-amino-4-chlorophenoxy)benzyl alcohol, is useful as a smooth muscle antagonist.

The diacetate derivative of 2-(2-amino-4-chlorophenoxy)benzyl alcohol, namely, 2-(2-acetamido-4-chlorophenoxy)benzyl acetate, is additionally useful as a smooth muscle antagonist. This compound is conveniently prepared by contacting 2-(2-amino-4-chlorophenoxy)benzyl alcohol with acetic anhydride and pyridine.

The smooth muscle antagonist (antispasmodic) utility of 2-(2-amino-4-chlorophenoxy)benzyl alcohol and 2-(2-acetamido-4-chlorophenoxy)benzyl acetate is evident from the results of a standardized test for their capacity to antagonize the activity of bradykinin, prostaglandin $E_2$ ($PGE_2$) and/or acetylcholine. The procedure, carried out substantially as described by J. H. Sanner in *Arch. Intern. Pharmacodynamie*, 180, 46 (1969), is as follows: A female guinea pig weighing between 200 and 500 grams is sacrificed by cervical dislocation, whereupon the ileum is quickly removed and a 2 centimeter segment thereof mounted in a 5-ml tissue bath containing modified Tyrode solution and adapted to record isotonic contractions. The Tyrode solution, at 37° C. and constantly bubbled with a mixture of 95% oxygen and 5% carbon dioxide (v/v), consists of 8.046 grams of $MgCl_2.6H_2O$, 1.000 gram of $NaHCO_3$, 0.058 gram of $NaH_2PO_4.H_2O$, 1.000 gram of dextrose, and $H_2O$ q.s. 1 liter. Doses of bradykinin, $PGE_2$, and acetylcholine necessary to induce approximately equal submaximal contractions are experimentally determined, whereupon two sets of three (one for each agonist at the predetermined dose) such contractions are recorded at 4-minute intervals as controls. The modified Tyrode solution is immediately replaced by a solution or suspension of test compound therein, at 37° C. and bubbled as before, following which three sets of contractions induced by the three agonists at the predetermined doses are recorded, beginning 4 minutes after the second control recording and continuing at 4-minute intervals thereafter. The first of these three sets serves only to maintain the dosage timing until the tissue is in equilibrium with the test compound. The last two sets are compared with the two control sets, and a compound is considered active vis-a-vis a given agonist if the mean contraction induced thereby in the presence of compound is not more than 25% of the mean control contraction for that agonist. The initial screening dose in this test is ordinarily 30 mcg. per ml. At this dose, 2-(2-amino-4-chlorophenoxy)benzyl alcohol reduced the spasmodic effect of bradykinin by 92%, the effect of acetylcholine by 59%, and totally blocked the effects of $PGE_2$.

Those skilled in the art will recognize that observations of activity in standardized tests for particular biological effects are fundamental to the development of valuable new drugs, both veterinary and human.

The fermentation processes of the present invention are ordinarily carried out in the medium wherein the organisms are cultured. However, it is likewise possible to separate the fungal cells from the culture medium by centrifugation or other means and use the resultant cellular material to complement the fermentation. Also, the cells can be ruptured ultrasonically or otherwise to facilitate access to enzymes present, which can be isolated by filtration or extracted with a solvent such as acetone or water and substituted for the organism or cells thereof.

A nutrient medium is required for culture of the organism, that is, a medium containing assimilable nitrogen and carbon. An adequate supply of sterile air should be maintained therein, for example by exposing a large surface of the medium to the air, or preferably by passing it through the medium in quantities sufficient to support submerged growth.

Suitable nitrogen sources are those normally employed for the purpose, including soy bean meal, corn steep liquor, cotton seed meal, meat extract, protein (optionally digested), peptone, yeast extract, distillers' solubles, casein hydrolysate, nitrate, and/or ammonium compounds. All of the foregoing materials with the occasional exception of the last two serve also as carbon sources. Other carbon containing substances satisfactory and conventionally used as nutrients are the carbohydrates, for example, glycerol, glucose, fructose, sucrose, lactose, maltose, inositol, dextrin, starch, and whey, among which inositol is additionally useful due to its unusual capacity to stimulate growth.

Phosphate, magnesium, and/or ferrous ions likewise may be incorporated in the culture medium as growth-promoting factors, if desired; buffers may be added to assure that growth is initiated at a substantially neutral pH; and wetting agents may be employed to improve contact between the compound and the fermenting agent. The addition of an anti-foaming agent is usually beneficial where isolated cells or enzymes are used to induce fermentation rather than the intact and growing organism, nutrients need not, of course, be present, but in either event, the medium is customarily preponderantly aqueous.

Concentration of the oxazepine substrate in the medium, as also fermentation time and temperature, can vary widely. Such operation conditions are to a certain extent interdependent. A preferred, but acritical, range of concentrations of the substrate is 0.01 − 10.0%, while fermentations of from 2 hours to 10 days duration at temperatures between 24° and 35° C. are representative. Obviously, conditions must not be such as to degrade the oxazepine, kill the organism prematurely, or inactivate the involved enzymes.

In a preferred embodiment of the invention, a nutrient medium containing about 3% oxazepine of substrate is aerobically incubated at 23° − 25° C. with a culture of the desired organism for a period of 1 − 3 days. The desired products are extracted with dichloromethane and isolated by chromatography.

Alternatively, the novel compound 2-(2-amino-4-chlorophenoxy)benzyl alcohol may be chemically produced by a two-step synthesis. The first step involves the reduction of 2-(2-nitro-4-chlorophenoxy)benzaldehyde following the procedure of Borch et. al., *J.A.C.S.*, 93, 2897 (1971) using sodium cyanoborohydride as the reducing agent. The resulting 2-(2-nitro-4-chlorophenoxy)benzyl alcohol is then catalytically hydrogenated using Raney nickle to afford the desired 2-(2-amino-4-chlorophenoxy)benzyl alcohol. This hydrogenation is conveniently conducted in a solvent, the choice of solvent depending upon the particular starting material employed. Generally speaking, a wide variety of solvents, such as alkanols wherein the alkyl portion contains 1 to 7 carbon atoms (e.g., methanol, ethanol and 2-propanol), ethyl acetate, and mixtures containing these solvents can be used. A particularly preferred solvent for this reaction is 50:50 ethanol-ethyl acetate. The reaction is generally conducted at a temperature ranging from room temperature to 100° C., with a temperature range of room temperature to 50°–60° C. being typical.

The following examples describe in detail processes illustrative of the present invention. It will be apparent to those skilled in the art that many modifications, both of materials and methods, may be practiced without departing from the purpose and intent of this disclosure. Throughout the examples hereinafter set forth, temperatures are given in degrees Centigrade (° C.), and relative amounts of materials in parts by weight, except as otherwise noted.

EXAMPLE 1

A culture of Hormodendrum sp. NRRL 8133 is grown initially for 14 days on potato dextrose agar (Difco) slants. Then, the spores and mycelia from a single slant are used to inoculate a 500 ml. seed flask containing 100 ml. of cottonseed meal medium (Pharmamedia, Traders Oil Mill Co.). The seed flask is incubated for a further 7 days at 23° – 25° C. on a rotary shaker at 190 rpm (3 cm. diameter stroke). 25 ml. of the growth from seed flask is then used to inoculate 100 ml. of cottonseed meal medium in a 500 ml. flask. This flask is incubated on the shaker at 23° – 25° C. for 24 – 48 hours until good growth is obtained, and then 0.025 part of 8-chloro-10,11-dihydrodibenz[b,f][1,4]oxazepine in 0.79 part acetone is added. Incubation is continued for 24 hours at the end of which time the culture broth is extracted three times with methylene chloride. The methylene chloride extracts are combined, dried over anhydrous sodium sulfate, and stripped to dryness in vacuo.

The methylene chloride residue is dissolved in ethyl acetate and chromatographed on silicic acid using a 5:95 ethyl acetate-n-hexane mixture as eluant. Removal of the solvent affords a crude product. Recrystallization of this product from benzene affords 8-chloro-10,11-dihydrodibenz[b,f][1,4]oxazepin-11-one, melting at 250° – 255° C. with decomposition and represented by the following structural formula.

Elemental analysis of this compound shows C, 67.84%; H, 3.67%; Cl, 15.94%; and N, 6.02%. The calculated values are: C, 67.98%, H, 3.51%; Cl, 15.44% and N, 6.10%. Further elution using 10:90 ethyl acetate-n-hexane mixture affords 2-(2-amino-4-chlorophenoxy)benzyl alcohol. This compound is further purified by high speed liquid chromatography using a 50:50 ethyl acetate-n-heptane mixture as eluant. This compound is represented by the following structural formula

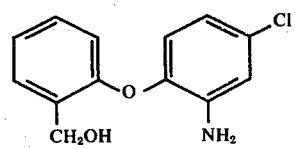

and exhibits infrared absorption maxima at 3620, 3500, 3410, 1623, 1610 and 1593 cm$^{-1}$. The nuclear magnetic resonance spectra exhibits chemical shifts at δ4.61 (J=5.55Hz), δ5.12 (J=5.5Hz) and δ5.28. Elemental analysis shows C, 62.50%; H, 5.13%; Cl, 14.64%, N, 5.27%. The calculated values are C, 62.53%, H, 4.84%; Cl, 14.20%; and N, 5.61%.

EXAMPLE 2

A culture of Hormodendrum cladosporioides NRRL 8132 is grown initially for 14 days on potato dextrose agar slants. The spores and mycelia from a single slant are used to inoculate a 500 ml. seed flask containing 100 ml. of cottonseed meal medium. After further incubation for 7 days at 23° – 25° C. on a rotary shaker at 190 rpm, 25 ml. of the growth is used to inoculate 100 ml. of cottonseed meal medium in a 500 ml. flask. This flask is then incubated at 23° – 25° C. for 24 – 48 hours on the shaker until good growth is evident. A solution of 0.025 part of 8-chloro-10,11-dihydrodibenz[b,f][1,4]oxazepine in 0.79 part acetone is added and incubation continued for an additional 48 hours. The culture broth is extracted three times with portions of methylene chloride. The methylene chloride extracts are combined, dried over anhydrous sodium sulfate, and stripped to dryness in vacuo. The residue is dissolved in ethyl acetate and chromatographed on silica gel using a 3:97 ethyl acetate-methylene chloride mixture as eluant. Recrystallization of the crude product affords 8-chlorodibenz[b,f][1,4]oxazepine melting at 73° – 73.5° C. and represented by the following structural formula.

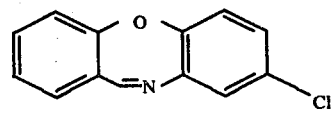

The spectral properties of the crude material eluted from the column evidence the existence of the hydroxy-amine intermediate, 8-chloro-10,11-dihydrodibenz[b,f][1,4]oxazepine-11-ol, of the following structural formula.

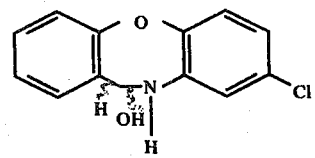

However, this compound is not isolatable.

EXAMPLE 3

When Trichoderma lignorum NRRL 8138, Cladosporium lignicolum NRRL 8131, Pullularia pullulans NRRL 8137, Penicillium sp. NRRL 8136, Mucor sp. NRRL 8135, Chaetomium sp. NRRL 8130, or Hormo-

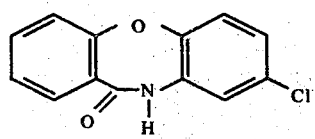

dendrum sp. NRRL 8134 are substituted for the Hormodendrum sp. NRRL 8133 of Example 1 and the procedure detailed in the first paragraph therein substantially repeated, there is obtained 2-(2-amino-4-chlorophenoxy)benzyl alcohol after chromatography on silica gel using a 10:90 ethyl acetate-n-hexane mixture or a 2:98 ethyl acetate-methylene chloride mixture as eluant, or chromatography on silicic acid using a 20:80 ethyl acetate-n-hexane mixture as eluant. Final purification is accomplished by high speed liquid chromatography using a 50:50 ethyl acetate-n-hexane mixture to give a product identical to that of the second paragraph of Example 1.

EXAMPLE 4

10 Parts 2-(2-nitro-4-chlorophenoxy)benzaldehyde and 2.4 parts sodium cyanoborohydride is dissolved with stirring in a mixture of 22 parts of tetrahydrofuran, 20 parts methanol and 10 parts by volume 2,2,2-trifluoroethanol. To the resulting mixture is added a trace of methyl orange and a sufficient amount of 2 N hydrochloric acid in methanol to attain a deep red color. Stirring is continued for approximately 24 hours at which time the solvents are removed in vacuo. The red, oily residue is dissolved in water and ethyl ether, and the ether layer separated. The water layer is extracted three times with 18 parts portions of ethyl ether. The ether extracts are combined with the ether layer, and extracted once with 50 parts of water. The ether is removed in vacuo to give crude 2-(2-nitro-4-chlorophenoxy)benzyl alcohol which is purified by chromatography.

0.3 Part of 2-(2-nitro-4-chlorophenoxy)benzyl alcohol is dissolved in 50 parts by volume of a 1:1 ethanol-ethyl acetate mixture and placed in a Parr bottle. A small amount of Raney nickel catalyst is added and the mixture is shaken at room temperature and a pressure of about 2 psi for approximately 9.5 hours. The catalyst is then removed by filtration and the filtrate is concentrated under reduced pressure to give a yellow-brown oil. Purification of the oil results in 2-(2-amino-4-chlorophenoxy)benzyl alcohol, identical to the product of the second paragraph of Example 1.

EXAMPLE 5

0.026 Part of 2-(2-amino-4-chlorophenoxy)benzyl alcohol is dissolved in 0.5 part pyridine and 0.5 part by volume acetic anhydride and allowed to stand at room temperature for 16 hours. The solvent is removed by evaporation under a nitrogen atmosphere and the resultant residue chromatographed on 0.6 part silicic acid. Elution with a 5:95 mixture of ethyl acetate-benzene and recrystallization from a mixture of ethyl acetate and benzene affords 2-(2-acetamido-4-chlorophenoxy)benzyl acetate. This compound melts at about 83° – 84° C. and is represented by the following structural formula.

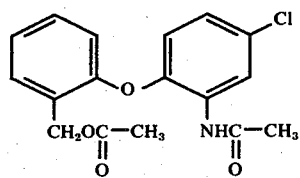

Elemental analysis shows C, 61.71%; H, 5.30%; Cl, 10.73%; N, 4.01%. The calculated values are C, 61.17%; H, 4.83%, Cl, 10.62%; and N, 4.20%.

What is claimed is:

1. A process for the preparation of 8-chloro-10,11-dihydrodibenz[b,f][1,4]oxazepine-11-one which comprises fermenting 8-chloro-10,11-dihydrodibenz[b,f][1,4]oxazepine with Hormodendrum sp. NRRL 8133 or enzymes therefrom in a suitable nutrient medium.

2. A process for the preparation of 8-chlorodibenz[b,f][1,4]oxazepine which comprises fermenting 8-chloro-10,11-dihydrodibenz[b,f][1,4]oxazepine with *Hormodendrum cladosporioides* NRRL 8132 or enzymes therefrom in a suitable nutrient medium.

* * * * *